United States Patent
Dearden et al.

(10) Patent No.: US 11,872,144 B2
(45) Date of Patent: Jan. 16, 2024

(54) SKIN PATCHES FOR SENSING OR AFFECTING A BODY PARAMETER

(71) Applicant: THE ALFRED E. MANN FOUNDATION FOR SCIENTIFIC RESEARCH, Valencia, CA (US)

(72) Inventors: Brian R. Dearden, Pasadena, CA (US); John G. Petrovich, Valley Village, CA (US)

(73) Assignee: THE ALFRED E. MANN FOUNDATION FOR SCIENTIFIC RESEARCH, Valencia, CA (US)

(*) Notice: Subject to any disclaimer, the term of this patent is extended or adjusted under 35 U.S.C. 154(b) by 570 days.

(21) Appl. No.: 16/362,459

(22) Filed: Mar. 22, 2019

(65) Prior Publication Data

US 2019/0290455 A1 Sep. 26, 2019

Related U.S. Application Data

(60) Provisional application No. 62/647,129, filed on Mar. 23, 2018.

(51) Int. Cl.
*A61B 5/05* (2021.01)
*A61B 5/00* (2006.01)
(Continued)

(52) U.S. Cl.
CPC ............. *A61F 2/72* (2013.01); *A61B 5/0002* (2013.01); *A61B 5/296* (2021.01); *A61B 5/6833* (2013.01);
(Continued)

(58) Field of Classification Search
CPC ....... A61B 8/4245; A61B 5/0006; A61B 5/24; A61B 18/14; A61B 5/02055;
(Continued)

(56) References Cited

U.S. PATENT DOCUMENTS 4,112,941 A * 9/1978 Larimore ............... A61B 5/274
600/394
4,121,573 A 10/1978 Crovella
(Continued)

FOREIGN PATENT DOCUMENTS

WO 01/13778 A2 3/2001
WO 2015/187377 A1 12/2015
(Continued)

OTHER PUBLICATIONS

Pasquina, P. F., et al., First-in-Man Demonstration of Fully Implanted Myoelectric Sensors for Control of an Advanced Electromechanical Arm by Transradial Amputees, Journal of Neuroscience Methods, Apr. 15, 2015, 244: 85-93.

(Continued)

*Primary Examiner* — Joseph A Stoklosa
*Assistant Examiner* — Brian M Antiskay
(74) *Attorney, Agent, or Firm* — Lewis Roca Rothgerber Christie LLP

(57) ABSTRACT

Skin patch sensors for monitoring and/or affecting body parameters, with alignment, positioning and attachment using magnets. The repeated use of releasable adhesive layers to retain skin patch sensors on skin can cause skin irritation, which can be reduced by rotating a skin patch between attachment times around a magnetically coupled pivot point. Skin patch sensors can be configured with internal coils to inductively couple to external power transmitting and communications coils with solenoids in anti-Helmholtz configurations.

12 Claims, 10 Drawing Sheets

(51) Int. Cl.
  *A61F 2/72* (2006.01)
  *B25J 9/00* (2006.01)
  *A61B 5/296* (2021.01)
  *A61F 2/70* (2006.01)
(52) U.S. Cl.
  CPC ....... *B25J 9/0006* (2013.01); *A61F 2002/707* (2013.01)
(58) Field of Classification Search
  CPC .......... A61B 2018/00839; A61B 5/318; A61B 5/7282; A61B 5/287; A61N 5/0601; A61N 1/37
  See application file for complete search history.

(56) References Cited

U.S. PATENT DOCUMENTS

| | | | |
|---|---|---|---|
| 4,270,543 A * | 6/1981 | Tabuchi | A61B 5/274 600/396 |
| 4,352,960 A | 10/1982 | Dormer | |
| 5,168,874 A | 12/1992 | Segalowitz | |
| 5,203,330 A | 4/1993 | Schaefer | |
| 5,458,124 A | 10/1995 | Stanko | |
| 5,511,553 A | 4/1996 | Segalowitz | |
| 5,579,781 A | 12/1996 | Cooke | |
| 5,704,351 A | 1/1998 | Mortara | |
| 5,862,803 A | 1/1999 | Besson | |
| 6,814,706 B2 | 11/2004 | Barton | |
| 7,130,696 B2 | 10/2006 | Carter | |
| 8,343,079 B2 | 1/2013 | Bartol | |
| 8,449,469 B2 | 5/2013 | Banet | |
| 8,634,909 B2 * | 1/2014 | Zimmerling | A61N 1/36038 607/116 |
| 9,919,154 B2 * | 3/2018 | Lee | A61N 1/3758 |
| 10,646,712 B2 * | 5/2020 | Smith | A61N 1/086 |
| 2003/0109905 A1 | 6/2003 | Mok | |
| 2003/0149349 A1 | 8/2003 | Jensen | |
| 2005/0215916 A1 | 9/2005 | Fadem | |
| 2006/0122473 A1 | 6/2006 | Kill | |
| 2006/0155386 A1 | 7/2006 | Wells | |
| 2008/0203831 A1 * | 8/2008 | French | H02K 49/102 310/46 |
| 2008/0275327 A1 * | 11/2008 | Faarbaek | A61B 5/68335 600/382 |
| 2010/0030341 A1 | 2/2010 | Dietl | |
| 2010/0081895 A1 | 4/2010 | Zand | |
| 2010/0239648 A1 * | 9/2010 | Smith | A61F 13/00063 602/54 |
| 2010/0298687 A1 | 11/2010 | Yoo | |
| 2011/0028822 A1 * | 2/2011 | Beck | A61B 5/25 600/386 |
| 2011/0295100 A1 | 12/2011 | Hegde | |
| 2012/0191147 A1 | 7/2012 | Rao | |
| 2014/0128992 A1 | 5/2014 | Engeberg | |
| 2015/0080696 A1 * | 3/2015 | Wang | A61B 5/282 600/383 |
| 2015/0087892 A1 * | 3/2015 | Tourrel | A61N 1/37518 607/57 |
| 2015/0094558 A1 * | 4/2015 | Russell | A61B 5/0022 600/391 |
| 2015/0124566 A1 | 5/2015 | Lake | |
| 2015/0134080 A1 | 5/2015 | Roh | |
| 2015/0141784 A1 | 5/2015 | Morun | |
| 2015/0148641 A1 | 5/2015 | Morun | |
| 2016/0015280 A1 | 1/2016 | Hyde | |
| 2016/0015972 A1 | 1/2016 | Hyde | |
| 2016/0045134 A1 * | 2/2016 | Jensen | A61B 5/0006 600/377 |
| 2016/0175600 A1 | 6/2016 | Amir | |
| 2017/0007427 A1 | 1/2017 | Zheng | |
| 2017/0007489 A1 | 1/2017 | Lin | |
| 2017/0136265 A1 | 5/2017 | Hyde | |

FOREIGN PATENT DOCUMENTS

| | | |
|---|---|---|
| WO | 2016/196675 A1 | 12/2016 |
| WO | 2017165410 A1 | 9/2017 |

OTHER PUBLICATIONS

Merrill, D.R., et al., Development of an Implantable Myoelectric Sensor for Advanced Prosthesis Control, Artificial Organs, Mar. 2011, 35(3): 249-252.

Hefferman, GM, et al., Integration of surface electromyographic sensors with the transfemoral amputee socket: A comparison of four differing configurations, Prosthetics and Orthotics International 2015, vol. 39(2) 166-173.

International Search Report and Written Opinion, International Application No. PCT/US19/23736, dated Jul. 16, 2019.

Mei, Henry, Coupled Resonator Based Wireless Power Transfer for Bioelectronics. Purdue Thesis, 2016. Chapter 3.

Australia Notice of Acceptance for Patent Application dated Feb. 4, 2022 issued in corresponding Australia Application No. 2019238325, 3 pages.

Canadian Examination Report for Application No. 3,094,526, dated Jun. 30, 2022, 3 pages.

Canadian Examination Report for Application No. 3,094,526, dated Apr. 5, 2023, 3 pages.

* cited by examiner

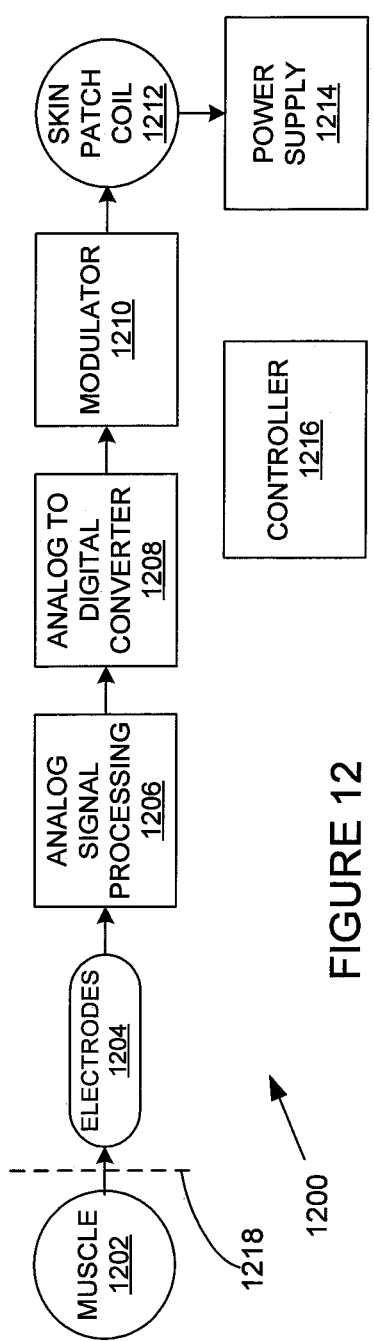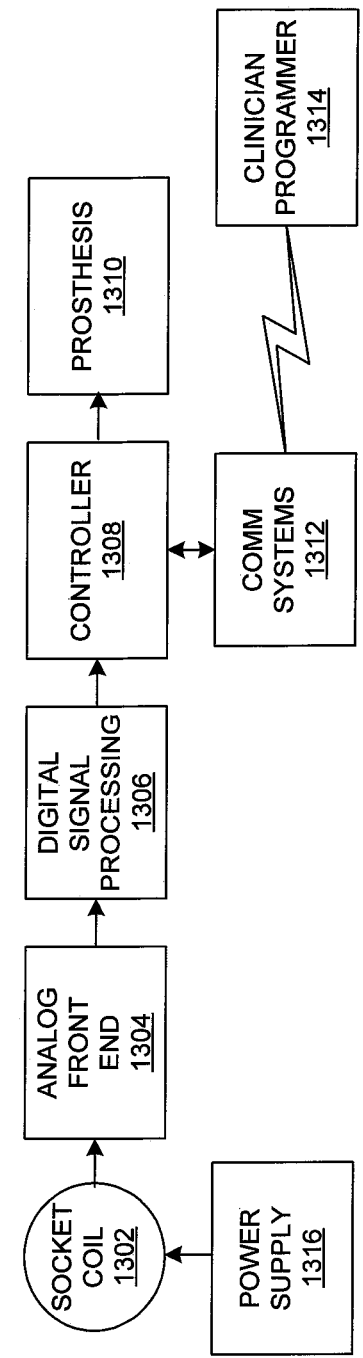

SKIN PATCHES FOR SENSING OR AFFECTING A BODY PARAMETER

CROSS REFERENCE TO RELATED APPLICATIONS

The present application claims benefit under 35 U.S.C. § 119(e) to U.S. Provisional Application Ser. No. 62/647,129, filed on Mar. 23, 2018 which is incorporated herein by reference in its entirety.

BACKGROUND

It is estimated that there are over 1 million people in the United States with limb loss. Various prosthetic devices have been developed to assist persons with such limb loss. Commercial systems available to date have relied on surface electromyographic (EMG) sensors with limited success, due to the difficulty of obtaining reliable muscle activity data from surface EMG sensors. Recent clinical trials of a system developed by The Alfred E, Mann Foundation For Scientific Research have shown the many advantages of an Implantable Myoelectric Sensor System (IMES™) using implanted myoelectric sensors. See Pasquina, P. F., et al, First-in-Man Demonstration of Fully Implanted Myoelectric Sensors for Control of an Advanced Electromechanical Arm by Trans-radial Amputees, Journal of Neuroscience Methods, 2015, April 15, 244: 85-93 and Merrill, D. R., et al, Development of an Implantable Myoelectric Sensor for Advanced Prosthesis Control, Artificial Organs, 2011, March, 35(3): 249-252.

Surface EMG sensors for prosthetic control are less expensive than implantable EMG sensors and may be more practical for the control of prosthetics as pattern recognition software is developed to interpret the multiple surface EMG signals received in order to properly move the prosthetic limb. EMG sensors can be used in medical systems for various applications, such as for example, measuring parasternal EMG signals in patients with chronic obstructive pulmonary disease (COPD) in order to determine their neural respiratory drive (NRD). See for example, US patent application publication 2013/0310699. Improved surface EMG sensors and systems would also enable the development and use of powered exoskeletons for therapy and rehabilitation of patients with mobility impairing ailments such as Parkinson's, multiple sclerosis, stroke and other medical conditions. See for example US patent application publications 2015/0134080 and 2017/0007489. Improved surface EMG sensors could also be useful for the control of strength enhancing exoskeletons for use in military and industrial applications.

SUMMARY

Skin patch sensors for monitoring and/or affecting body parameters, with alignment, positioning and attachment using magnets. The repeated use of releasable adhesive layers to retain skin patch sensors on skin can cause skin irritation, which can be reduced by rotating a skin patch between attachment times around a magnetically coupled pivot point. Skin patch sensors can be configured with internal coils to inductively couple to external power transmitting and communications coils with solenoids in anti-Helmholtz configurations.

BRIEF DESCRIPTION OF THE DRAWINGS

FIG. 12 is a block diagram of systems in an exemplary skin patch.

FIG. 13 is a block diagram of an exemplary system for controlling a prosthesis using data signals from one or more skin patches.

DETAILED DESCRIPTION

Figure 1:
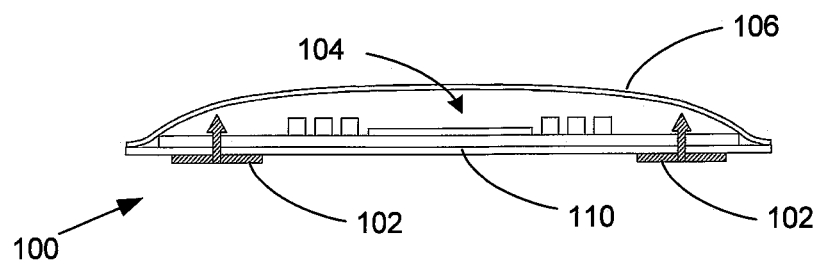
FIG. 1 is a cross sectional side view of a wireless skin patch for sensing or affecting a body parameter.

FIG. 1 is a cross sectional side view of a wireless flexible skin patch 100 for sensing or affecting a body parameter. In some embodiments, skin patch 100 is sensing electromyographic (EMG) signals. Skin patch 100 includes electrodes 102, electronic components 104 on a flexible circuit board, flexible cover 106 and is mounted on flexible adhesive substrate 110. Electronic components 104 include one or more coils or antennas for inductively coupling the skin patch to an external power transmitting and communications coil. The electrodes may be made of stainless steel or other metal suitable for use as an electrode to which a disposable electrode may be attached, such as adhesive get type electrodes commonly used for ECG sensing. The disposable electrodes may be part of adhesive substrate 110. The electrodes could also be a micro-array made of metal or silicon that pierces the outer layers of skin in order to reduce the impedance of the interface and to improve the signal strength of the sensed electrical signals. The electrodes may also be a needle electrode, configured for injection into the skin, either subdermally for improved signal strength or deeper into a targeted muscle for selectivity and signal strength. When using needle electrodes, they could be of the bipolar type or monopolar and used in combination with a surface electrode built into adhesive substrate 110. In some embodiments, the skin patch may be configured and positioned on the skin of a person to sense other electrical signals, such as electrocardiographic (ECG) or electroencephalographic EEG signals.

In some embodiments, a skin patch 100 may incorporate other sensors such as temperature sensors, accelerometers, gyroscopes, inertial measurement units, or reflectance type blood oximetry sensors to measure blood oxygen and pulse rate. An inertial measurement unit made of a 3 axis accelerometer and a 3 axis gyroscope, when attached to skin in various chest locations on a person, can sense many parameters such as: respiration rate and strength, cardiac monitoring, patient posture and activity and fall detection.

In some embodiments, the skin patch may be configured and positioned on the skin of a person to generate transcutaneous electrical nerve stimulation (TENS) for therapeutic purposes. More than one coil can be in skin patch 100 and may have various configurations such as a planar or spiral coil, as will be discussed with regard to FIG. 2 or one or more solenoid coils, either discrete coils or part of the flex circuit, positioned for inductive coupling with an external coil providing external RF for wireless power transmission to the skin patch. A coil or coils within skin patch 100 and an external coil have to be properly oriented to each other to maximize the coupling coefficient between the coils for maximum efficiency and to maximize the immunity of the link to changes in the coupling coefficient. For example, the solenoid coils in multiple skin patches 100 in various positions around a residual limb may couple with a solenoid coil in a prosthetic socket with all of the axes of the solenoid coils substantially parallel to each other for the maximum coupling between the coils. Wireless communications with skin patch 100 may be based on a variety of methods, such as, for example, load modulation of the wireless power transmission to the skin patch 100. Such wireless communications may also include near field (NFC), Bluetooth or other communications protocols. The operating parameters of skin patch 100 may be controlled by wireless communications from a terminal controller (not shown) operated by a physician or technician or from a patient operated remote control (not shown).

The adhesive substrate 110 includes two layers of adhesive, one layer of adhesive on one side to releasably mount the substrate to the skin patch and a second layer of adhesive on the opposite side of the substrate to releasable mount the skin patch 100 to skin. Substrate 100 may be made of paper or a flexible layer of plastic for improved adhesion to curved surfaces of skin such as on an arm or a leg. In some embodiments, skin patch 100 is made with a flexible base and cover to provide the ability to be flexed upon adhesive mounting to better conform to the curvature of the limb to which it is attached, to provide a lower profile and for improved signal capture. In some embodiments, the substrate is a layer of compressible foam to provide a better fit for the skin patch to the curvature of the limb to which it is attached. In some embodiments, adhesive gel electrodes are incorporated into the adhesive substrate. In some embodiments, the skin patch is powered by a rechargeable or primary battery, where the primary battery may be changed by a user or by a technician. If the skin patch is powered by a rechargeable battery, the rechargeable battery can be charged wirelessly or through a wired connection.

Figure 2:
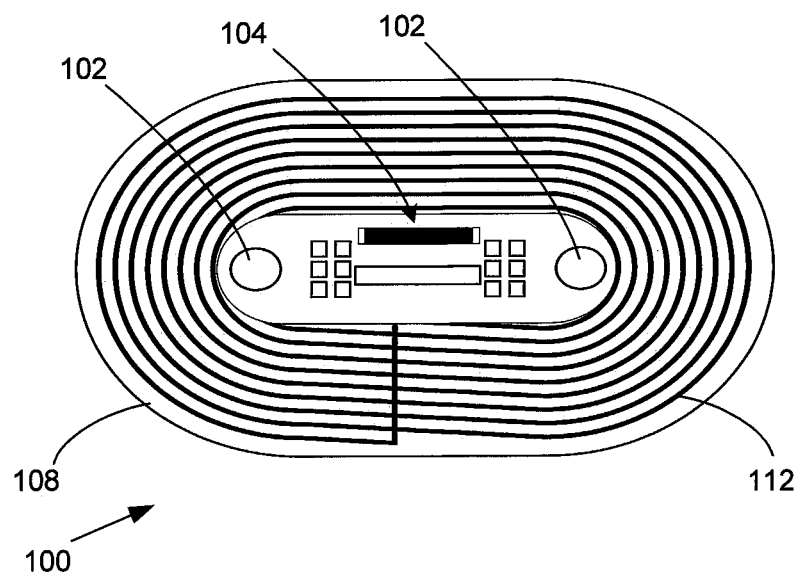
FIG. 2 is a top view of a wireless skin patch for sensing or affecting a body parameter.

FIG. 2 is a top view of a wireless skin patch 100, shown without a cover, for sensing or affecting a body parameter. Skin patch 100 includes base 108, electrodes 102, electronic components 104 and planar or spiral coil 112. Skin patch 100 may be releasably attached to skin by an adhesive substrate as discussed with regard to FIG. 1. Spiral coil 112 may be inductively coupled to an external planar coil or to a pair of solenoids in an anti-Helmholtz configuration as will be discussed with regard to FIG. 11.

Figure 3:
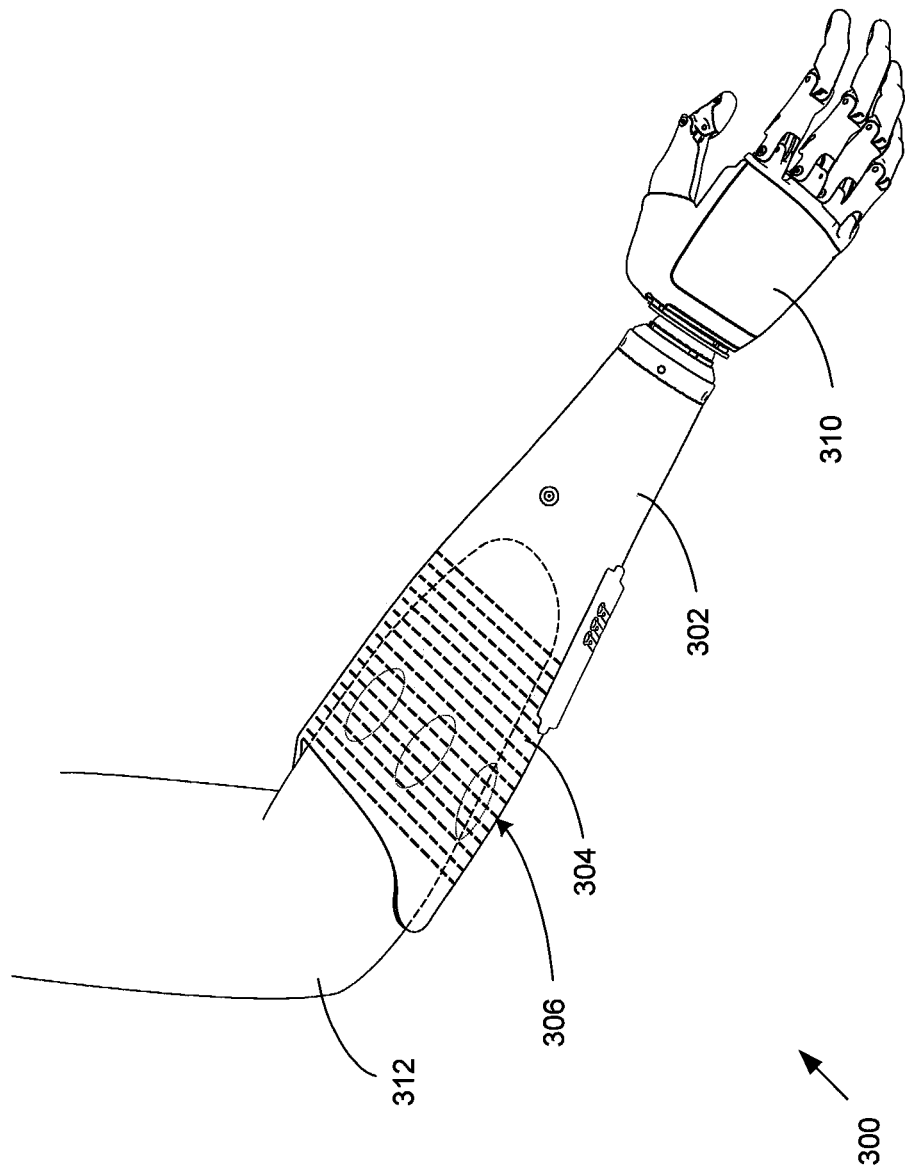
FIG. 3 is a view of part of a system for EMG control of a prosthetic limb.

FIG. 3 is a view of part of a prosthesis control system 300 for EMG control of a prosthetic limb. Residual limb 312 is coupled to system 300 and includes prosthetic socket 302 and prosthesis 310. Several skin patch EMG sensors 306 monitor multiple EMG signals in residual limb 312 and transmit EMG data signals to prosthesis control system 300. Prosthesis control system 300 includes solenoid 304 for transmitting alternating current to power EMG sensors 306 and for bidirectional communications with EMG sensors 306. Prosthetic socket 302 includes electronic systems, such as a power supply, a controller, analog and digital signal processing to receive the multiple EMG data signals from skin patches 306 to generate motion control commands, which are sent to a prosthesis controller. The prosthesis controller is connected to and actuates the motion of prosthesis 310. The operating parameters of prosthesis control system 300 may be controlled by wireless communications from a terminal controller (not shown) operated by a physician or technician or from a patient operated remote control (not shown). The electronic systems of the prosthesis system 300 are discussed with respect to FIG. 11.

Figure 4:
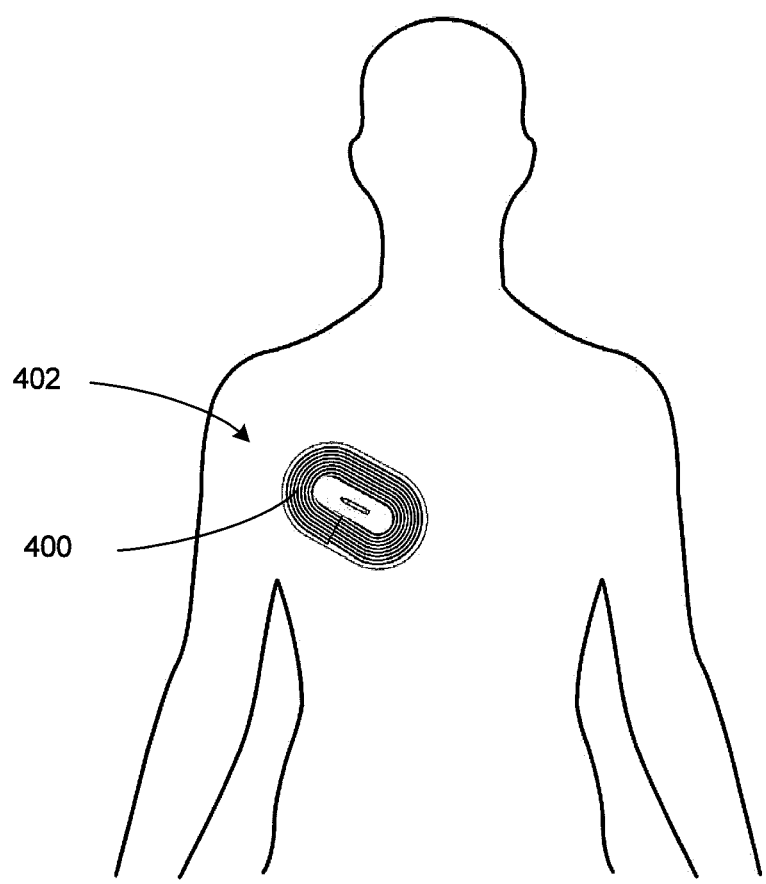
FIG. 4 is a view of a wireless skin patch sensor positioned on a patient's chest.

FIG. 4 is a view of a wireless skin patch 400 positioned on a patient's chest 402. As was described with respect to skin patch 100, skin patch 400 may be any one of a variety of sensors such as EMG, ECG or a motion sensor using an inertial measuring unit.

Figure 5:
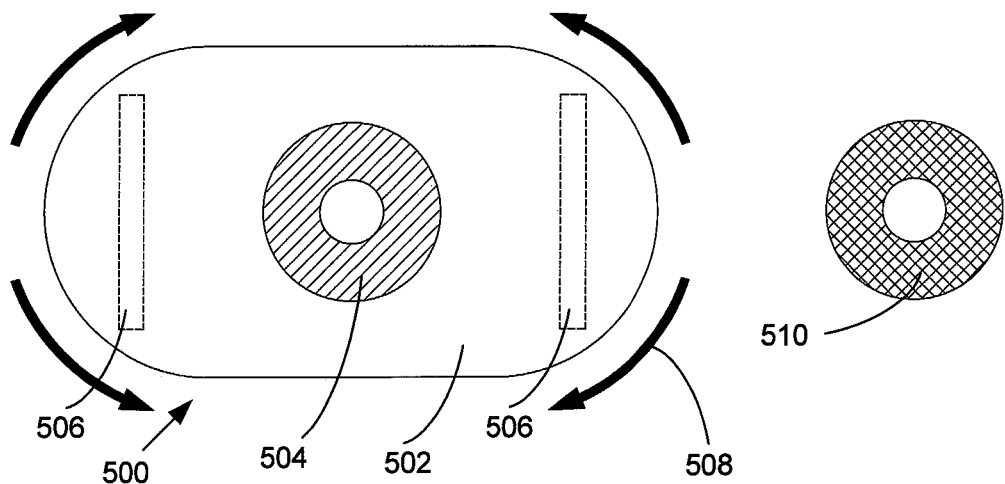
FIG. 5 is a top view of a skin patch with magnetic alignment features.

FIG. 5 is a top view of a skin patch 500 with magnetic alignment features. Skin patch 500 includes base 502, circular magnet 504 and optional longitudinal magnets 506. The arrows 508 indicate that skin patch 500 may be rotated around the pivot point defined by implanted element 510 in between repeated attachments of skin patch 500 to the same general skin location. Other aspects of skin patch 500, such as the electronic components and coil are not shown to simplify this figure. Circular element 510 is a ferromagnetic element for implantation below the skin as an alignment point for repeated positioning of skin patch 500 to the same location on skin. After element 510 is implanted below the skin, skin patch 500 is positioned in proximity to element 510 and magnet 504 magnetically couples to element 510 and skin patch 500 can be attached to that section of skin where element 510 is located, using an adhesive substrate, such as was described with respect to FIG. 1. In some embodiments, element 510 is a magnet and is oriented such that after implantation, it magnetically couples to magnet 504 at the time of the attachment of skin patch 500 to the skin location defined by the implanted element 510. In some embodiments, skin patch 500 includes additional magnets 506 which can also be used for the alignment of skin patch 500 to a skin location using implanted magnets 602 as shown in FIG. 6.

After skin patch 500 has been attached at a skin location and is later detached from the skin location, a new adhesive substrate can be attached to skin patch 500. Then skin patch 500 can be positioned above implanted element 510 using the magnetic coupling between magnet 504 and implant 510 to align skin patch 500 with the skin location and skin patch 500 can be rotated as indicated by arrows 508 about a pivot point defined by implant 510. This can reduce the amount of skin used for such repeated attaching of skin patch 500 and thus reduce skin irritation.

Figure 6:
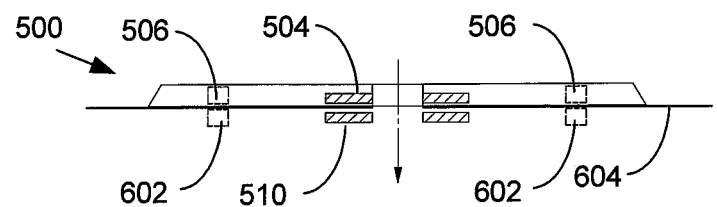
FIG. 6 is a cross sectional side view of a skin patch with magnetic alignment features.

FIG. 6 is a cross sectional side view of skin patch 600 retained on skin 604 with magnetic alignment features. Skin patch 500 includes base 502, circular magnet 504 and optional longitudinal magnets 506. Shown implanted below the skin 604 are element 510 and optional ferromagnetic elements 602, which in some embodiments are magnets. Magnets 504 and 506 are used for alignment with elements 510 and 602 and skin patch 500 can be held in position on the skin using an adhesive substrate. In some embodiments, elements 510 and 602 are magnets and the magnetic coupling and the attractive forces between the magnets 504 and 506 above the skin, and the magnets 510 and 602 below the skin, can be sufficient to keep skin patch 500 in position on the skin, even if no adhesive substrate is used to retain skin patch 500 on the skin. The central aperture in magnet 504 can be used to provide an opening for one or more electrodes in some embodiments.

Figure 7:
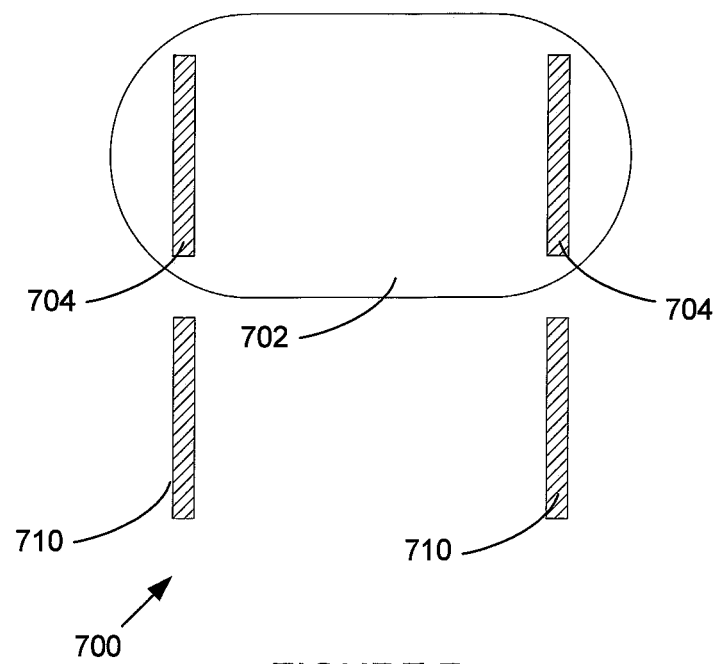
FIG. 7 is a top view of a skin patch with magnetic positioning features.

FIG. 7 is a top view of skin patch 700 with magnetic positioning features. Skin patch 700 includes base 702 and longitudinal magnets 706 and is similar to skin patch 500 in FIG. 5, except that there is no central magnet 504, which provides more space for various sensors in the center of skin patch 700. Elements 710 are ferromagnetic elements for implantation below the skin as alignment points for repeated positioning of skin patch 700 to the same location on skin. In some embodiments, elements 710 are magnets.

Figure 8:
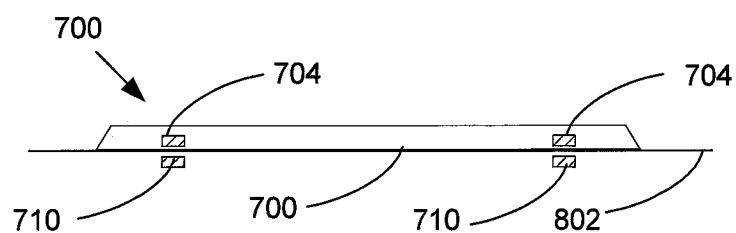
FIG. 8 is a cross sectional side view of a skin patch with magnetic positioning features.

FIG. 8 is a cross sectional side view of skin patch 800 retained on skin 802 with magnetic positioning features. Skin patch 700 includes base 702 and longitudinal magnets 704. Shown implanted below the skin 802 are ferromagnetic elements 710, which in some embodiments can be magnets. Magnets 704 are used for alignment with elements 710 and skin patch 700 can be held in position on the skin using an adhesive substrate. In some embodiments, elements 710 are also magnets and the attractive forces between the magnets 704 above the skin, and the magnets 710 below the skin, can be sufficient to keep skin patch 700 in position on the skin, even if no adhesive substrate is used to retain skin patch 700 on the skin.

Figure 9:
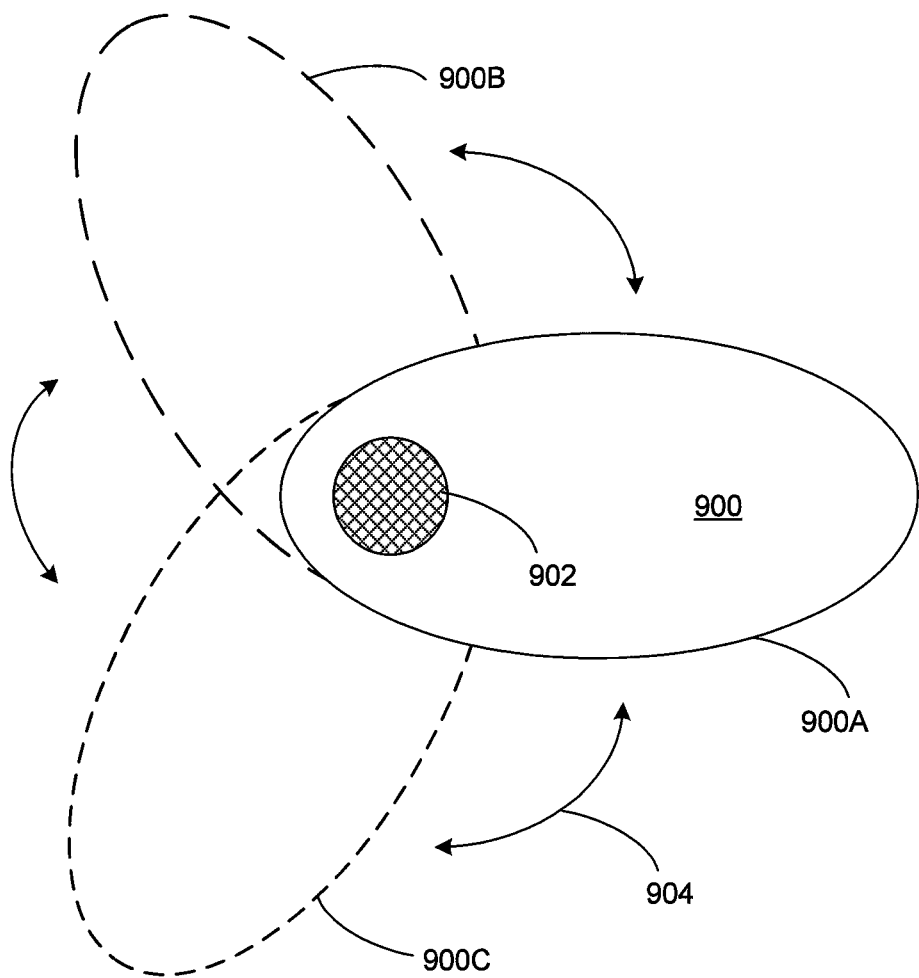
FIG. 9 is a view of several possible positions for a skin patch as it is rotated around a pivot point.

FIG. 9 is a view of several possible positions for skin patch 900 as it is rotated, around a pivot point defined by magnet 902 offset from the center of the skin patch, and an implanted ferromagnetic element just below the position of magnet 902, which is not shown in FIG. 9. For example, skin patch 900 can be in position 900A for an adhesive attachment to the skin location underneath and after skin patch 900 is detached from the skin, it can be reattached via rotation as indicated by arrows 904 at location 900B or 900C or any other position that can be reached by rotation around a pivot point defined by the magnetic coupling of magnet 902 to an implanted ferromagnetic element below magnet 902. Such rotation between attachments to the same general skin location will reduce the amount of skin exposed to adhesives and thus reduce the area size of any resultant skin irritation. Magnet 902 may have any of a variety of polygon type shapes and be configured with or without a central aperture.

Figure 10A:
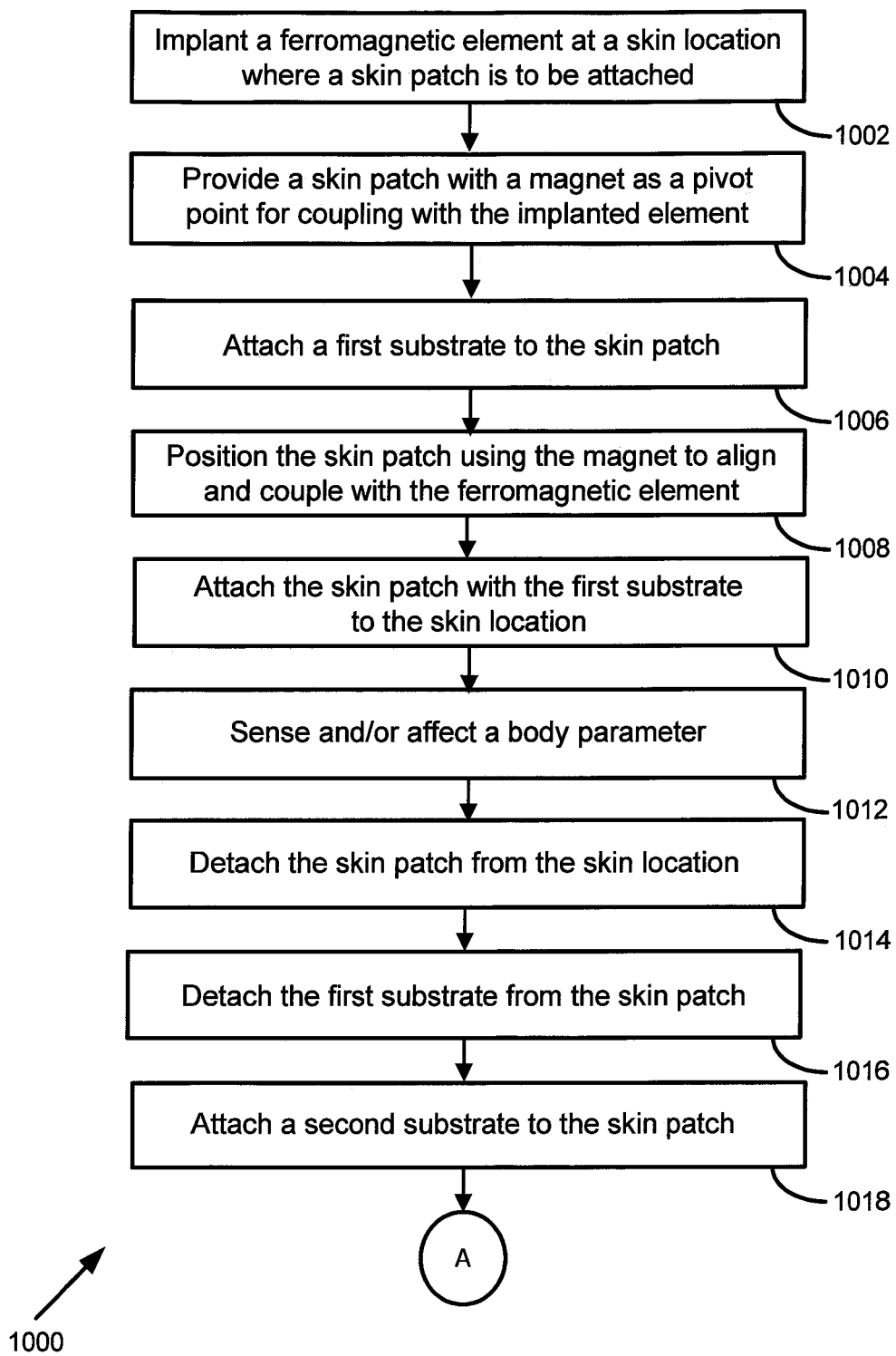
FIGS. 10A and 10B are flow charts of a method for releasably attaching a skin patch with first and second substrates with reduced skin irritation.
Figure 10B:
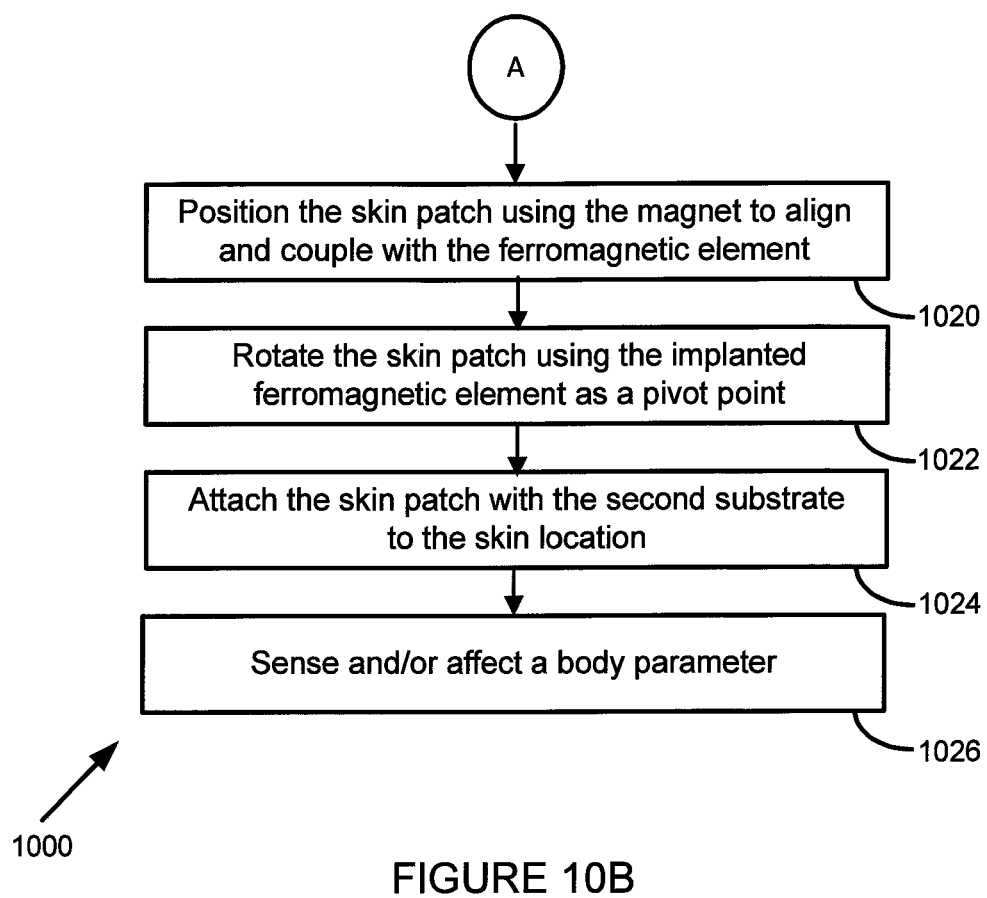

FIGS. 10A-10B illustrate a flow chart of a method 1000 for releasably attaching a skin patch with first and second substrates to the same general skin location at different times. Exemplary method 1000 can apply to the skin patches shown in FIGS. 5-9. In block 1002, a ferromagnetic element is implanted subcutaneously at a skin location. In block 1004, a skin patch is provided for sensing and/or affecting a body parameter. The skin patch has a magnet configured to align with and magnetically couple to the implanted element. In block 1006, a first substrate is attached to the bottom of the skin patch. The first substrate has a first surface with an adhesive coating for releasable attachment to the bottom surface of the skin patch. The first substrate has a second surface with an adhesive coating on the second layer of the first substrate for releasable attachment to the skin location. In block 1008, the skin patch is positioned at the skin location with the implanted ferromagnetic element in alignment with the magnet and with magnetic coupling between the magnet and the implanted ferromagnetic element.

In block 1010, the skin patch is attached to the skin location with the first substrate. In block 1012, the skin patch is used to sense or affect a body parameter. In block 1014, the skin patch is detached from the skin location. In block 1016, the first substrate is detached from the skin patch. In block 1018, a second substrate is attached to the skin patch. The second substrate has a first surface with an adhesive coating for releasable attachment to the bottom surface of the skin patch. The second substrate has a second surface with an adhesive coating on the second layer of the second substrate for releasable attachment to the skin location.

In block 1020, the skin patch is positioned at the skin location with the implanted ferromagnetic element in alignment with the magnet and with magnetic coupling between the magnet and the implanted ferromagnetic element. In block 1022, the skin patch is rotated using the implanted ferromagnetic element as a pivot point. This reduces the amount of skin being reattached to each time and results in a smaller area of irritated skin. In block 1024, the skin patch is attached to the skin location using the second substrate. In block 1026, the skin patch is used to sense or affect a body parameter. This process 1000 can be repeated as needed by repeating steps 1014 to 1026 with subsequent adhesive substrates and rotating the skin patch as needed each time before reattaching the skin patch to the same general skin location to reduce the area of irritated skin.

Figure 11:
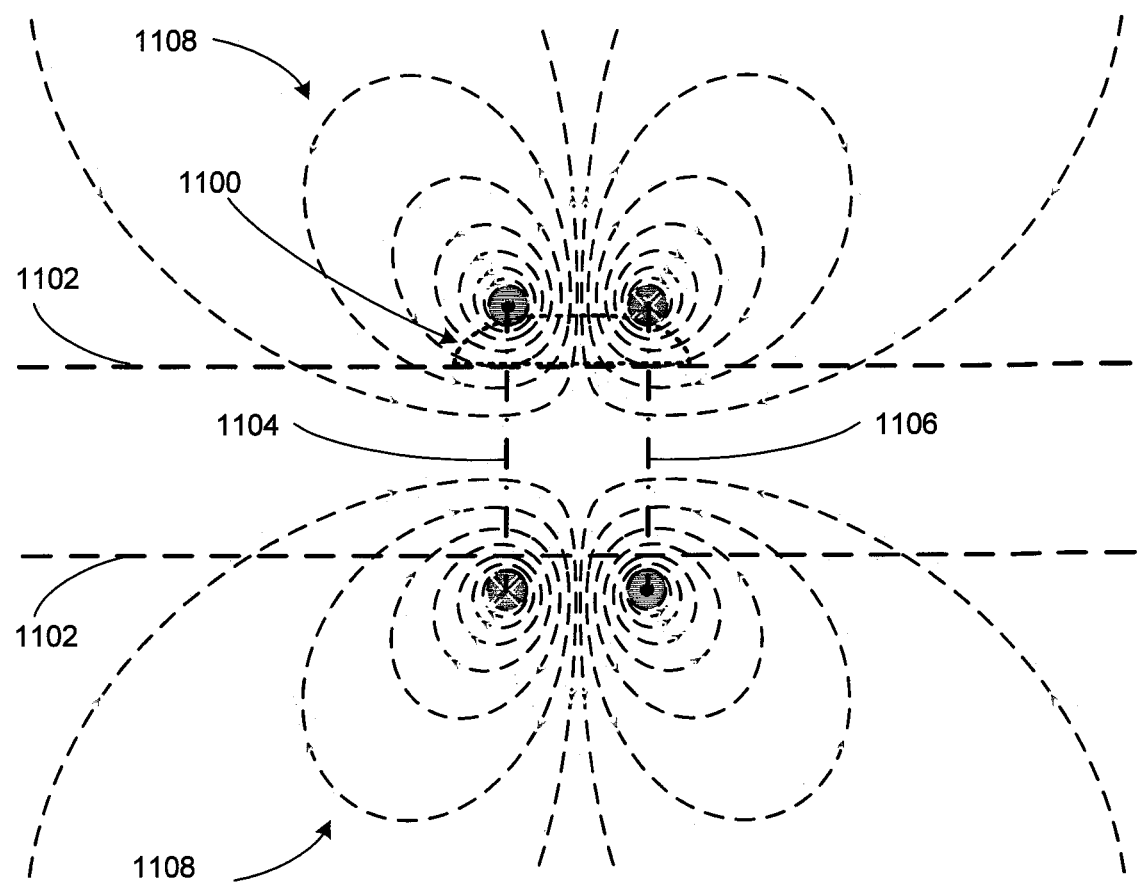
FIG. 11 is a diagram showing an outline of a limb with a skin patch wirelessly powered by a pair of solenoids in an anti-Helmholtz configuration.

FIG. 11 is a diagram showing the outline of skin patch 1100 mounted on limb 1102 and wirelessly powered by a pair of solenoids 1104 and 1106 in an anti-Helmholtz configuration. In an anti-Helmholtz configuration, two solenoids are positioned along the same axis with the current flow in each solenoid being opposite to the current flow in the other solenoid. The distance between the solenoids is equal to the radius of the solenoids. In the center of the space between the solenoids, the magnetic field is zero, but the magnetic field is not zero away from the center and varies as is shown by the approximate field lines 1108. Skin patch 1100 has an internal planar or spiral coil, similar to coil 112 in FIG. 2, and this internal spiral coil is inductively coupled to the non-zero magnetic field generated by the solenoid coils 1104 and 1106 near to the surface of limb 1102. An anti-Helmholtz solenoid configuration can wirelessly power a number of skin patches 1100 positioned on the surface of a limb 1102. In some embodiments, skin patch 1100 has an internal solenoid oriented for inductive coupling for power transfer from external solenoids in an anti-Helmholtz configuration.

FIG. 12 is a block diagram of systems in an exemplary skin patch 1200 for EMG sensing. Skin patch 1200 can be similar to the skin patches described with respect to FIGS. 1-3 and 4-9. Skin patch 1200 is positioned on a skin location and senses EMG signals from muscle 1202 through skin 1216 using electrodes 1204. The electrodes 1204 are connected to an analog signal processing system 1206, which is connected to an analog to digital converter (ADC) 1208. The output of ADC 1208 is modulated by modulator 1210, the output of which is connected to skin patch coil 1212. Coil 1212 operates as an antenna to transmit the processed EMG signals to a prosthesis control system, such as described with regard to FIGS. 3 and 13, or in some embodiments, to an exoskeleton control system. In some embodiments, coil 1212 receives RF power signals which are coupled to power supply 1214 for powering skin patch 1200 and for recharging a rechargeable battery. Controller 1216 generates command signals to the various systems in skin patch 1200. Controller 1216 may be a microcontroller, a microprocessor, or a state machine. Power supply 1214 may include a primary or rechargeable battery.

FIG. 13 is a block diagram of an exemplary prosthesis control system 1300 for controlling a prosthesis or an exoskeleton using EMG data signals from one or more skin patches, for example, as was described with respect to FIG.

3 and FIG. 12. Socket coil 1302 may be wirelessly coupled to coil 1212 of skin patch 1200 in FIG. 12 to receive EMG data signals. In some embodiments, coil 1302 is connected to power supply 1316 and transmits an RF signal to a skin patch for power transmission. Coil 1302 is connected to analog front end 1304 for demodulating the received EMG data transmission from a skin patch 1200. The demodulated output of analog front end 1304 is connected to digital signal processing 1306 for recovery of the sensed EMG data. The output of digital signal processing 1306 is connected to controller 1308, which generates motion commands to prosthesis 1310 or to an exoskeleton. Controller 1308 is connected to communications systems 1312 to provide an RF link, such as NFC, Bluetooth or other communications protocol to external devices such as a clinician programmer 1314 or a remote control (not shown). In one embodiment, a control system similar to prosthesis control system 1300 may control an exoskeleton using several skin patches 100.

What is claimed is:

1. A skin patch being:
  for releasable attachment to a skin location of a patient, the skin patch comprising:
    a housing comprising a base for supracutaneous attachment to the skin location and a cover covering the base;
    at least one ferromagnetic element for subcutaneous implantation below the skin location;
    at least one magnet to position the skin patch at the skin location by magnetic coupling with the at least one ferromagnetic element, the at least one magnet being in the housing and affixed to the base and defining an aperture therewithin;
    at least one electrode for sensing a body parameter and/or for affecting a body parameter, the at least one electrode being on the base and located in the aperture of the at least one magnet;
    an antenna coupled to the at least one electrode and to receive wireless power transmissions for powering the skin patch;
    additional magnets at opposing ends along a longitudinal axis of the housing, adjacent to the at least one magnet, and to align the skin patch to the skin location, the additional magnets being strip shaped in a direction crossing the longitudinal axis of the housing;
    additional ferromagnetic elements for subcutaneous implantation below the skin location and to position the skin patch at the skin location by magnetic coupling with the additional magnets, the additional ferromagnetic elements being strip shaped to correspond to the additional magnets,
    wherein the antenna comprises a radio frequency (RF) coil.

2. The skin patch of claim 1, wherein the radio frequency (RF) coil is a spiral coil.

3. The skin patch of claim 1, further comprising a substrate or releasably attaching the skin patch to the skin location, the substrate having first and second opposite facing surfaces, and the substrate comprises:
  an adhesive coating on a first layer of the substrate for releasable attachment to the skin patch; and
  an adhesive coating on a second layer of the substrate for releasable attachment to the skin location.

4. The skin patch of claim 1, wherein the at least one ferromagnetic element is a pivot point for rotation of the skin patch.

5. A system for controlling a prosthetic limb or an exoskeleton comprising:
  the skin patch according to claim 1, wherein the at least one electrode comprises a plurality of electrodes for sensing electromyographic (EMG) signals in a residual limb or a limb coupled to the exoskeleton, wherein the plurality of electrodes is coupled to a transmitter, and the transmitter is configured to transmit a data signal corresponding to sensed EMG signals via the antenna;
  optionally at least one of the plurality of electrodes comprises at least one of: a needle electrode or a silicon electrode; and
  a controller configured for coupling to the residual limb or to the limb coupled to the exoskeleton, the exoskeleton comprising:
    an antenna for receiving the data signal from the skin patch, the antenna to transmit wireless power to the skin patch;
    a receiver coupled to the antenna for processing the received data signal;
    a transmitter coupled to the antenna for communications with the skin patch; and
    the controller coupled to the receiver for generating a plurality of motion control commands for the prosthetic limb or the exoskeleton,
  wherein the prosthetic limb or the exoskeleton is coupled to the controller and configured to receive and respond to the motion control commands.

6. The system of claim 5, wherein the antenna of the controller comprises a plurality of solenoids in an anti-Helmholtz configuration for inductively coupling alternating current to the skin patch.

7. A skin patch being:
  for multiple releasable attachments to a skin location of a patient,
  the skin patch comprising:
    a housing comprising a base for supracutaneous attachment to the skin location and a cover covering the base;
    at least one ferromagnetic element for subcutaneous implantation below the skin location;
    at least one magnet for positioning the skin patch at the skin location by magnetic coupling with the at least one ferromagnetic element, the at least one magnet being in the housing and affixed to the base and defining an aperture therewithin;
    at least one electrode for sensing a body parameter and/or for affecting a body parameter, the at least one electrode being on the base and located in the aperture of the at least one magnet;
    an antenna coupled to the at least one electrode for providing at least one of the following:
      transmitting a wireless data signal corresponding to the sensed body parameter; and/or
      receiving commands from an external controller;
    a power supply for powering the skin patch;
    additional magnets at opposing ends along a longitudinal axis of the housing, adjacent to the at least one magnet, and to align the skin patch to the skin location, the additional magnets being strip shaped in a direction crossing the longitudinal axis of the housing; and
    additional ferromagnetic elements for subcutaneous implantation below the skin location and to position the skin patch at the skin location by magnetic coupling with the additional magnets, the additional ferromagnetic elements being strip shaped to correspond to the additional magnets.

8. The skin patch of claim 7, wherein the magnetic coupling between the at least one magnet and the at least one ferromagnetic element releasably attach the skin patch to the skin location.

9. The skin patch of claim 7, wherein the magnetic coupling between the at least one magnet and the at least one ferromagnetic element provide a pivot point for rotating the skin patch prior to a subsequent releasable attachment of the skin patch to the skin location.

10. The skin patch of claim 7, wherein the power supply of the skin patch consists of either: a primary battery or a rechargeable battery.

11. The skin patch of claim 7, wherein the antenna is configured to receive wireless power, and comprises at least one of:
- a spiral coil,
- a solenoid,
- a spiral coil configured to inductively couple to a plurality of solenoids in an anti-Helmholtz configuration or
- a solenoid configured to inductively couple to a plurality of solenoids in an anti-Helmholtz configuration.

12. The skin patch of claim 1, wherein the at least one magnet is inside the skin patch.

\* \* \* \* \*